United States Patent [19]
Danielian et al.

[11] Patent Number: 5,862,285
[45] Date of Patent: Jan. 19, 1999

[54] MULTICHANNEL OPTICAL FIBER BUNDLE WITH ORDERED STRUCTURE IN ITS SENSITIVE PROBE TIP

[75] Inventors: George L. Danielian, Moscow, Russian Federation; Wolfgang Neuberger, F.T.Labuan, Malaysia

[73] Assignee: Ceramoptec Industries, Inc., East Longmeadow, Mass.

[21] Appl. No.: 511,357

[22] Filed: Aug. 4, 1995

[51] Int. Cl.⁶ .................................................. C02B 6/06
[52] U.S. Cl. .............................................. 385/121; 385/116
[58] Field of Search ........................ 385/12, 115–121; 356/371, 373

[56] References Cited

U.S. PATENT DOCUMENTS

| | | | |
|---|---|---|---|
| 3,244,894 | 4/1966 | Steele et al. | 250/226 |
| 3,327,584 | 6/1967 | Kissinger | 382/321 |
| 3,328,143 | 6/1967 | Hicks, Jr. | 385/115 |
| 3,383,192 | 5/1968 | Siegmund | 385/117 |
| 3,586,562 | 6/1971 | Jones | 385/115 |
| 3,586,563 | 6/1971 | Fukami et al. | 385/115 |
| 3,669,639 | 6/1972 | Inoue et al. | 385/115 |
| 3,674,452 | 7/1972 | Strack | 385/116 |
| 3,702,275 | 11/1972 | Hooker, III | 385/116 |
| 5,136,674 | 8/1992 | Kakiuchi et al. | 385/121 |
| 5,155,790 | 10/1992 | Hwang | 385/121 |
| 5,453,838 | 9/1995 | Danielian et al. | 356/371 |
| 5,652,810 | 7/1997 | Tipton et al. | 385/12 |

*Primary Examiner*—Hung N. Ngo
*Attorney, Agent, or Firm*—Bolesh J. Skutnik; BJ Associates

[57] ABSTRACT

Multifunctional optical fiber bundles for image and signal transmission or sensor applications are proposed. The optical fiber bundles exhibit reduced speckle noise resulting from spatial inhomogeneity and asymmetry of radiation of specific fibers of the bundle. This is achieved by ordering of fiber positions in the bundle sensitive probe tips according to some prescribed rule.

18 Claims, 20 Drawing Sheets

ORDERED MULTI CHANNEL FIBER OPTIC BUNDLE

ORDERED MULTI CHANNEL FIBER OPTIC BUNDLE

SENSITIVE PROBE TIP WITH HEXAGONAL STRUCTURE

ORDERED MULTI CHANNEL FIBER OPTIC BUNDLE
HEXAGONAL STRUCTURE OF FIBERS

MODIFICATION 1

ORDERED MULTI CHANNEL FIBER OPTIC BUNDLE
HEXAGONAL STRUCTURE OF FIBERS

MODIFICATION 2

FIBER F0 FOR TRANSMITTING CHANNELS

FIBER F1-F4 FOR FOUR RECEIVING CH.

FIBER F5 FOR RECEIVING CHANNEL 5

FIBER F6 FOR RECEIVING CHANNEL 6

FIBER F7 FOR RECEIVING CHANNEL 7

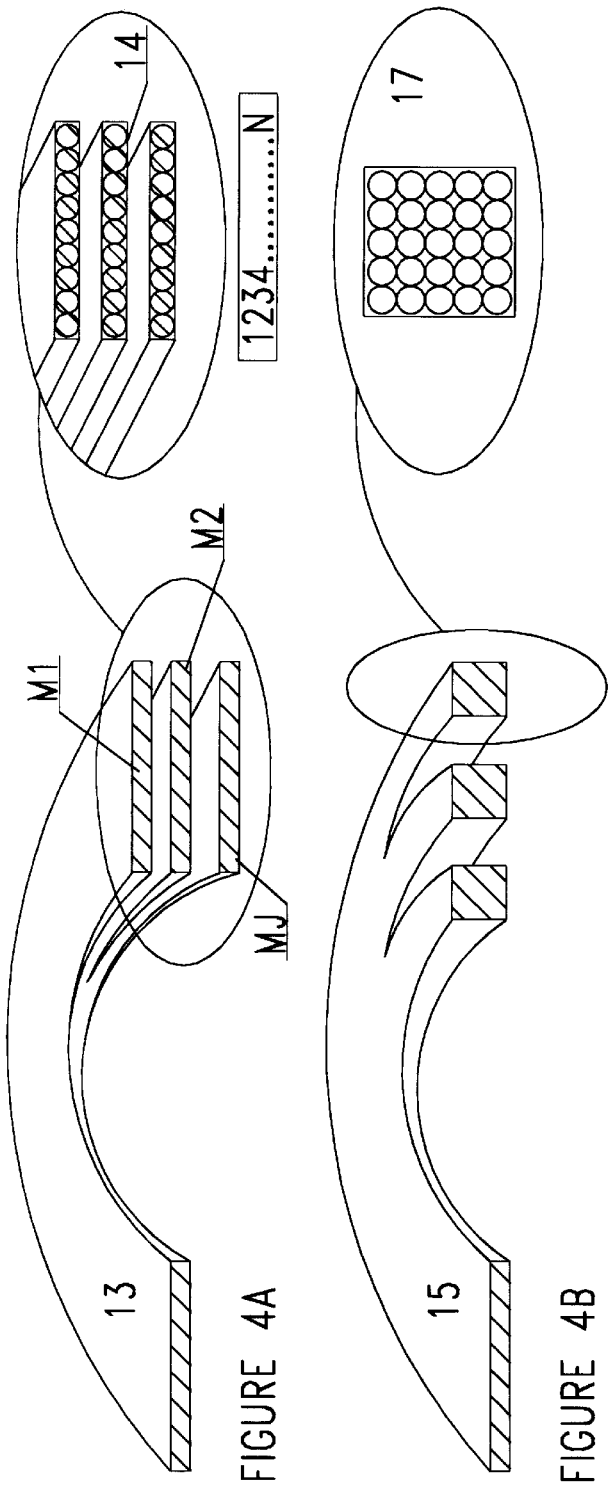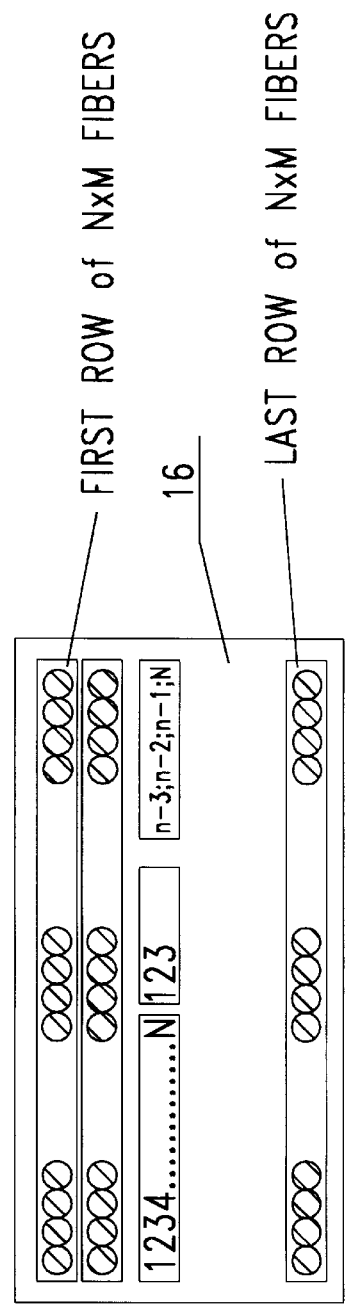
FIGURE 4A
FIGURE 4B
FIGURE 4C

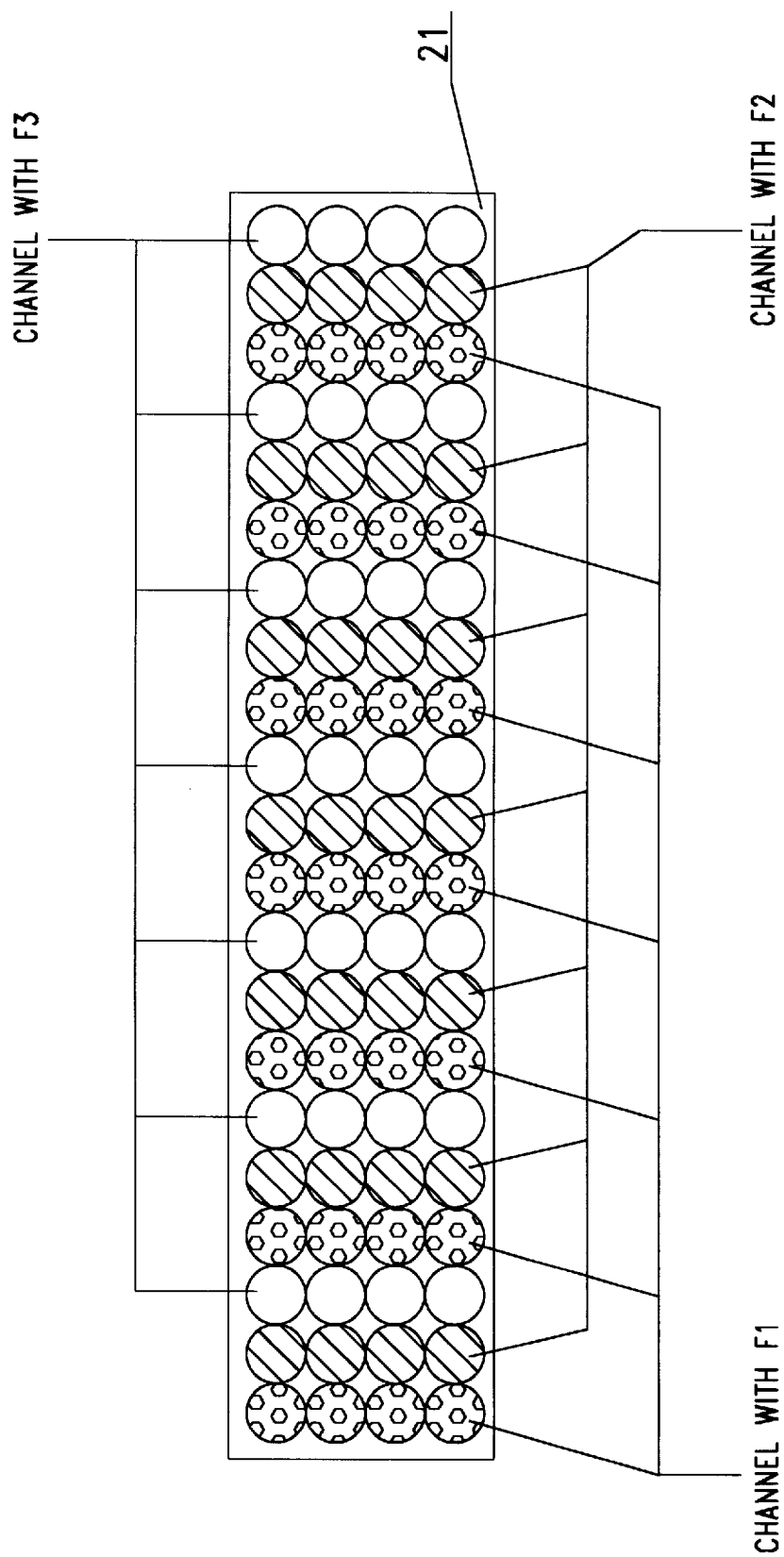

MULTICHANNEL OPTICAL FIBER BUNDLE WITH ORDERED STRUCTURE IN ITS SENSITIVE PROBE TIP

BACKGROUND OF THE INVENTION

1. Field of the Invention

The invention relates to multifunctional optical fiber bundles for image and signal transmission or sensor applications and particularly to a special kind of the bundles with reduced speckle noise (resulting from spatial inhomogeneity and asymmetry of radiation of specific fibers of the bundle) having ordered structure of fiber positions in its sensitive probe tip according to some prescribed rule.

2. Information Disclosure Statement

Multichannel optical fibers bundles provide very flexible tools for light transmission to and/or light receiving from some object. In general case such a bundles can be designed as a structure of fibers with prescribed positions of their ends in a sensitive probe tip bundled into specific light transmitting and light receiving channels.

Such bundles have many important applications. They can be used, for example, in various spectroscopic devices, process-photometers as a sensitive probe and light transmitting tool. Other applications of the bundles include high sensitive sensors of displacement or vibration measuring systems. Moreover, an ordered optical fiber bundle can be used as a light transmitting and reading device of raster type for linear detecting and light emitting components.

Many optical fiber bundles of various constructions have been designed and numerous methods of manufacturing of the bundles have been developed.

U.S. Pat. No. 3,244,894 describes photoelectric detection device utilizing randomized optical light conducting means which use a randomized single channel bundle.

U.S. Pat. No. 3,702,275 describes a fiber optic encoding-decoding apparatus and method for its fabrication. The apparatus employs an image encoding-decoding single channel bundle. The bundle is fabricated by steps of coiling the fiber into a thyroidal bundle of fiber convolutions. A randomization between fibers can be performed only for reproducing the image portion in random.

U.S. Pat. No. 3,383,192 describes a method of making fiberscope. It utilizes the fiber bundles that comprise a flexible structure of fibers.

U.S. Pat. No. 3,328,143 offers a method of making light-conducting optical multifiber structures which utilize a fiber optical image-transfer device.

U.S. Pat. No. 3,586,562 describes a method of making scrambled branched fiber optics. This method utilizes a mixed scrambling of branched fiber optic which is an initial layer of fibers on a drum of drawing machine. The fibers intermediate the tape strips are secured together by cement, and the fibers are then cut in the lacquered sections.

U.S. Pat. No. 3,674,452 claims a method of fabricating illuminated fiber optics. This method involves initially fabricating a fiber optic conduit, wherein a plurality of light-conducting fibers are formed in a bundle with a predetermined geometrical configuration at the first end and an identical geometrical configuration at the second end of the bundle.

U.S. Pat. No. 3,669,639 describes a method for production of a fused energy-conducting structure and also describes an apparatus for cementing a plurality of fibers in a simple parallel arrangement.

U.S. Pat. No. 3,586,563 offers a method for producing an optical fiber bundle by winding the fiber element onto a drum while it is rotated in one direction so that a layer of the helical wound windings is formed one channel structure on the drum.

U.S. Pat. No. 3,327,584 describes a fiber optic proximity probe, wherein transmitting and receiving fibers are bundled into channels with casual randomization ordering. The random numbers of transmitting or receiving fibers are placed snugly at the probe tip, wherein signals coming from the fibers near-by located fibers are mixed.

None of these inventions, however, discloses an optical fiber bundle whose fibers are arranged according to a programmable order in such a way that a plurality of fibers in the transmitting and receiving channels have spatial type of a layer or a matrix structure providing reduction of speckle noise and maximizing sensitivity as required for sensor and other applications. The speckle noise in each specific fiber is due to dynamic variation of spatially inhomogeneous speckle pattern resulting from the interference of many fiber modes. Collecting the radiation from many fibers included in the bundle can be used for averaging the speckle pattern and thus for reducing the speckle noise. Moreover, the modal noise in a multichannel optical fiber bundle, sensitivity of the signal on distance and angle between a reflecting surface, and the sensitive probe tip essentially depend on the specific structure in which the fiber ends of the optical bundle are ordered in its sensitive probe tip. For example, in optical fiber bundles with some specific ordering of the fiber in sensitive probe tip the sensitivity can be increased and the modal noise decreased in many times in comparison with nonordered bundle.

OBJECTS AND SUMMARY OF THE INVENTION

It is an object of the present invention to describe a multichannel optical fiber bundle comprising a plurality of optical fibers ordered in light transmitting and light receiving channels according to a special rule providing reduction of speckle noise and other useful properties of the bundle desirable for various sensors and image transmission applications.

It is a further object of the invention to eliminate the need for elaborate feed back control mechanisms.

Briefly stated, the present invention provides a multifunctional optical fiber bundle for image and signal transmission or sensor applications. The optical fiber bundle exhibits reduced speckle noise resulting from spatial inhomogeneity and asymmetry of radiation of specific fibers of the bundle. This is achieved by ordering of fiber positions in the bundle's sensitive probe tip according to some prescribed rule.

The above, and other objects, features and advantages of the present invitation will become apparent from the following description read in conjunction with the accompanying drawings.

BRIEF DESCRIPTION OF DRAWINGS

FIG. 4a shows an ordered multichannel optical fiber bundle having linear sensitive probe tip 13 and linear light transmitting and receiving channels 14.

FIG. 4b shows an ordered multichannel optical fiber bundle having linear sensitive probe tip 15 and matrix structure of light transmitting and receiving channels 17.

FIG. 4c shows a cross sectional view of a sensitive probe tip 16 ordered by two-dimensional logic into a multichannel optical fiber bundle with linear structural randomization.

FIG. 7b shows sensitive probe tip 21 of a raster type having three channels.

DESCRIPTION OF PREFERRED EMBODIMENTS

The present invention discloses an ordered flexible multichannel optical fiber bundle for optical signal transmission and remote sensing applications. The main feature of the ordered multichannel optical fiber bundle is a possibility of reducing speckle noise by special ordering of fiber positions inside the bundle.

The speckle noise in a system of light and dark light spots appearing in the beam coming from a coherent source of radiation (including laser diodes or monochromatic light sources of spectroscopic devices). It is a result of constructive and destructive interference depending on phase difference between rays incident at specific points of a light receiving optical surface. If the light is transmitted by an optical fiber, then the size of the speckles and their relative motion (speckle noise) depend on such different factors as small defects in fibers, variations in refractive index of fiber core and cladding, etc. In optical sensing systems the speckle noise results in a twinkle effect whenever it can be mixed with the main signal. One possible way of reducing the speckle noise is by averaging the phases of different light rays by providing each of them a different optical path length. The optical path length depends on both the fiber geometry and fiber length. Therefore, if the rays from a light transmitting fiber are collected by a group of symmetrically located light receiving fibers, then their relative phases can be averaged. The larger the sum aperture of all light receiving fibers and the more symmetrical their locations, the less the influence of the speckle noise on the received useful signal.

Multichannel optical fiber bundles having a hexagonal or linear structure of the fibers in their sensitive probe tip provide a possibility to reduce the speckle noise by using symmetry of light receiving fibers and also by using multichannel bundle structure for numerical analysis of received signals. Large number of receiving channels provides a possibility of considerably improving the signal/noise ratio. For example, in the case of two or more similar light receiving fibers one can realize numerical filtering of the signals, their correlation analysis or select useful signal by employing Fast Fourier Transform Analysis for correction of the signal spectra.

Figure 1A:
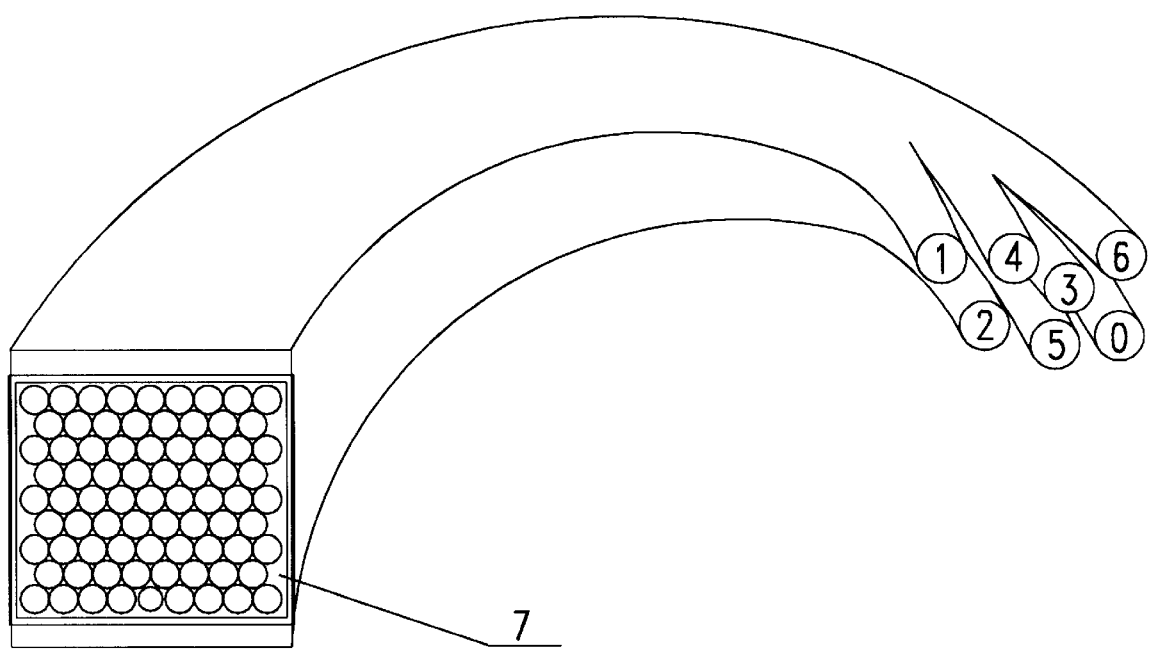
FIG. 1a shows a typical multichannel bundle of hexagonal type having one sensitive probe tip 7 and seven separate channels numbered from 0 to 6.
Figure 1B:
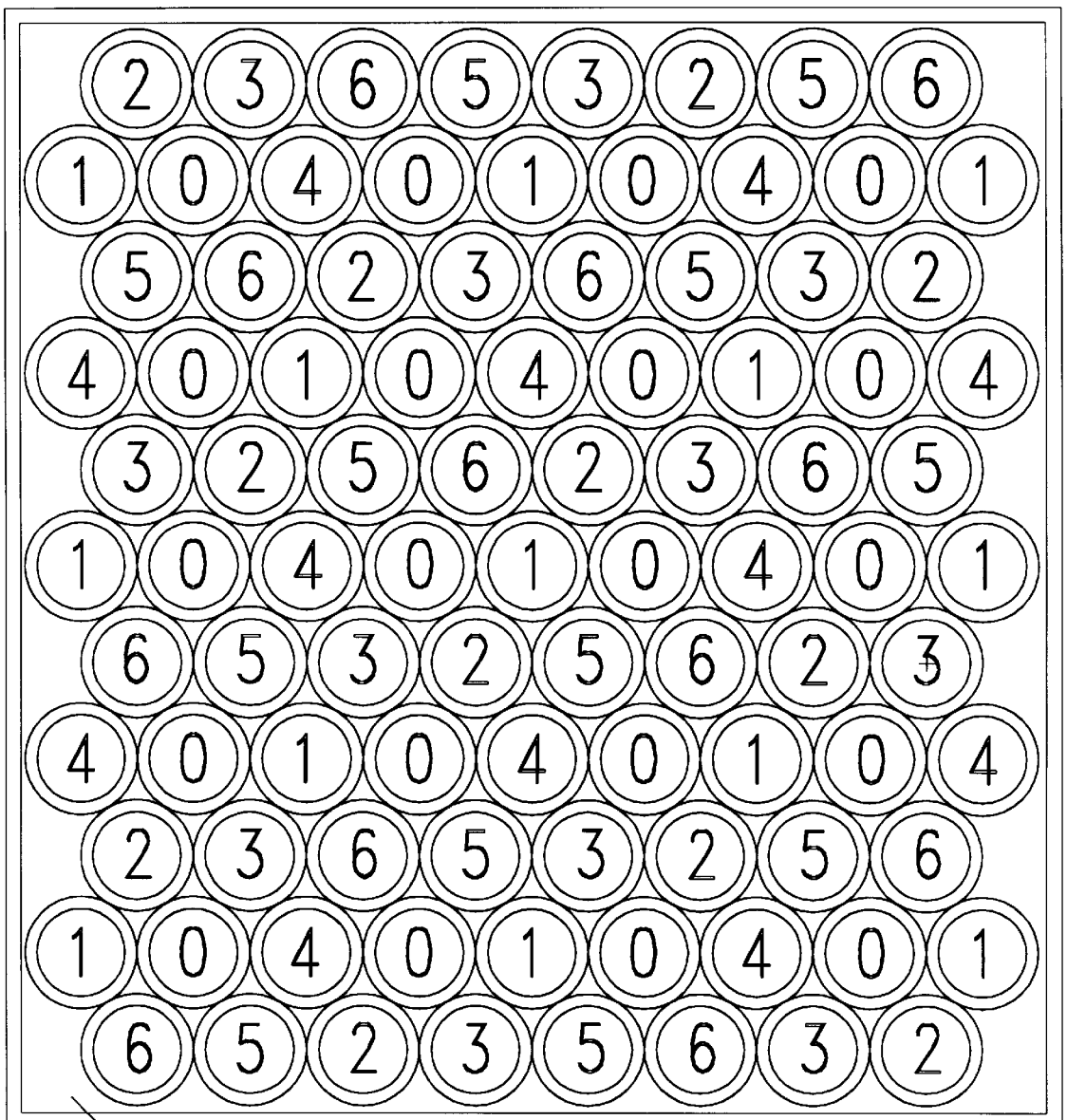
FIG. 1b shows a structure of sensitive probe tip 7 of an ordered multichannel fiber optic bundle.
Figure 1C:
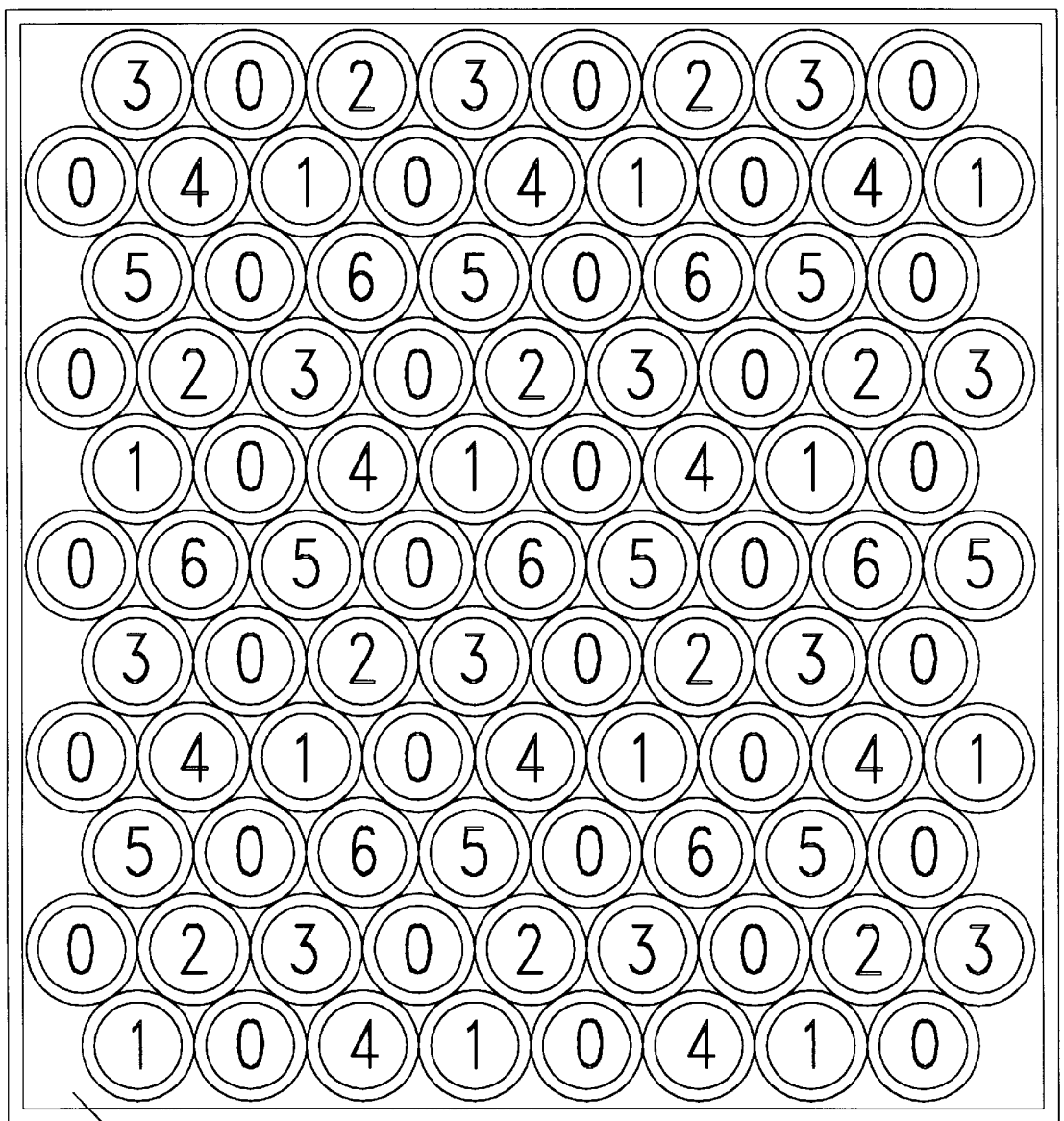
FIG. 1c shows another structure of sensitive probe tip 7 of an ordered multichannel fiber optic bundle.

Typical structure of such a bundle is shown in FIG. 1a. It generally comprises a sensitive probe tip 7, combining optical fibers with prescribed positions of their ends (randomized or ordered according to some prescribed rule) and at least two remote ends of the bundle comprising light transmitting and light receiving fiber channels. The multichannel optical bundle shown in FIG. 1a has one light transmitting (0) and six light receiving channels (1,2,3,4,5, 6). Seven optical fibers of the bundle are arranged in ordered hexagonal structure with rectangular cross section in sensitive probe tip 7 in such a way that each light transmitting fiber 0 is surrounded with six light receiving fibers (1–6) as shown in FIG. 1b. In the case shown in FIG. 1b each light receiving fiber is has two near-by light transmitting fibers while in the case of bundle shown in FIG. 1c each light receiving fiber has three near-by light transmitting fibers. The last case provides larger number of pairs including light transmitting and receiving fibers and better light transmitting performance for the given cross section of a bundle end tip. Thus, the difference between structures shown in FIG. 1b and in FIG. 1c is the number of light transmitting fibers and the number of light transmitting fibers coupled to each light receiving fiber. The structure shown in FIG. 1b can be used when it is desirable to have large sum aperture of light receiving fibers while the structure of FIG. 1c may be employed in the case when large number of light transmitting fibers and hence more intensive and homogeneous beam is required.

Figure 1D:
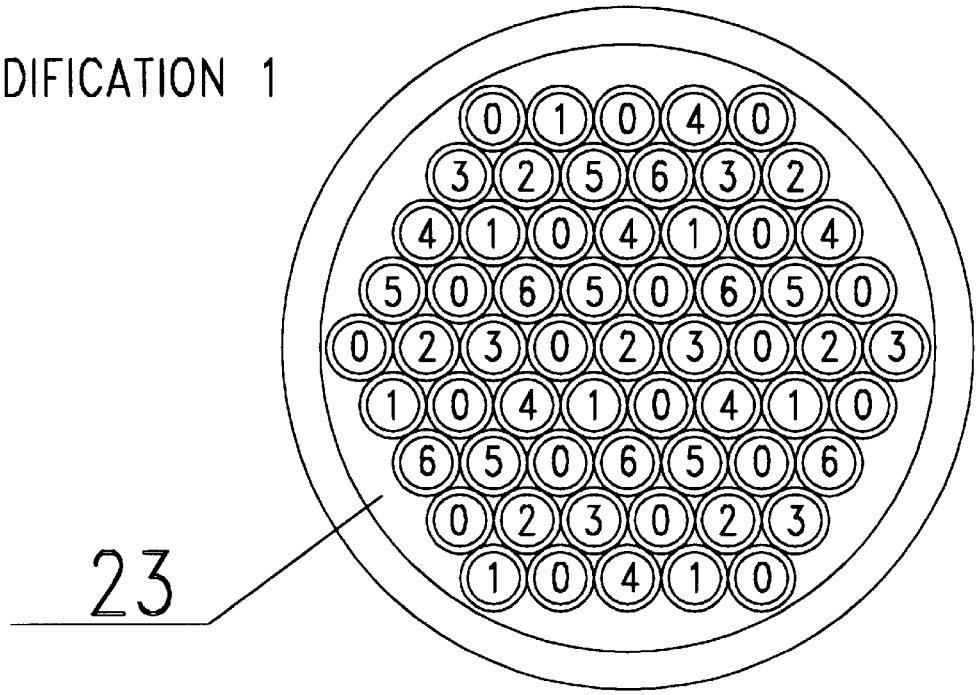
FIG. 1d shows a schematic of a hexagonal sensitive probe tip having circular sensitive probe tip 23 and comprising fibers of seven types (0,1,2,3,4,5,6).
Figure 1E:
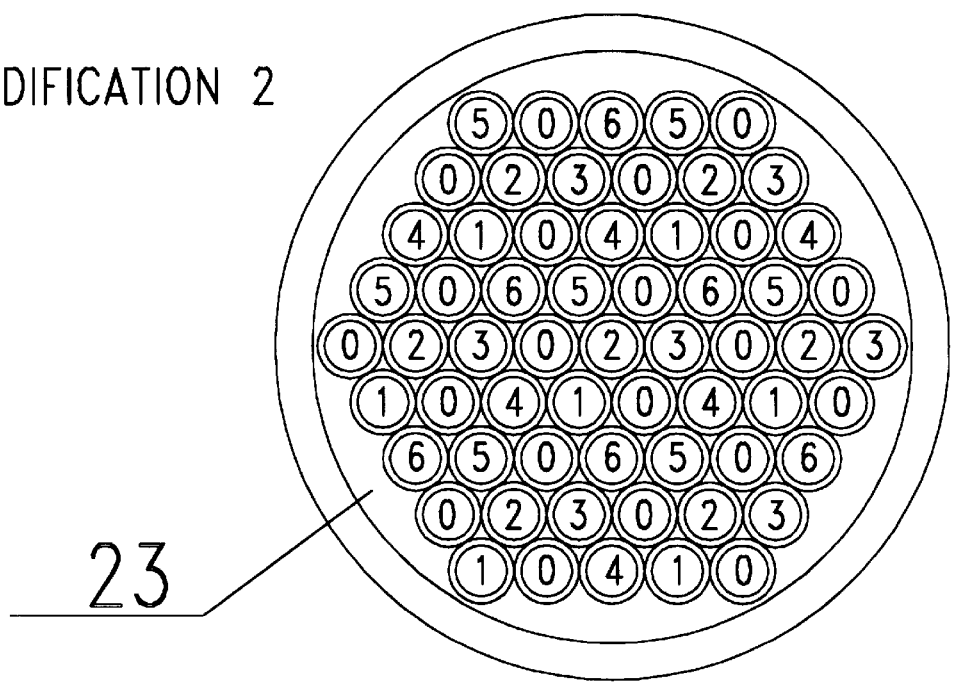
FIG. 1e shows a hexagonal sensitive probe tip of circular shape comprising fibers of three types (0,1,2).
Figure 1F:
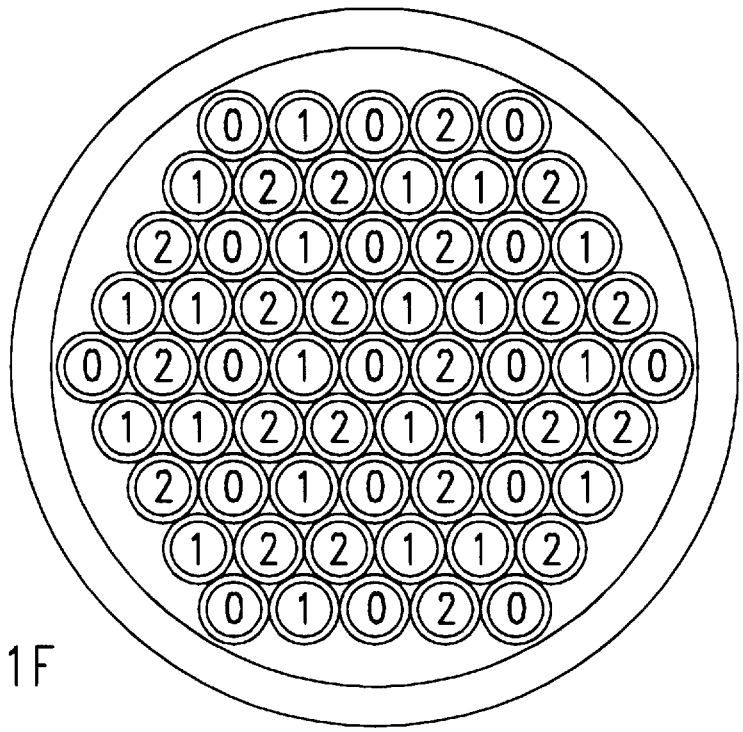
FIG. 1f shows a hexagonal sensitive probe tip of circular shape comprising fibers of four types (0,1,2,3).
Figure 1G:
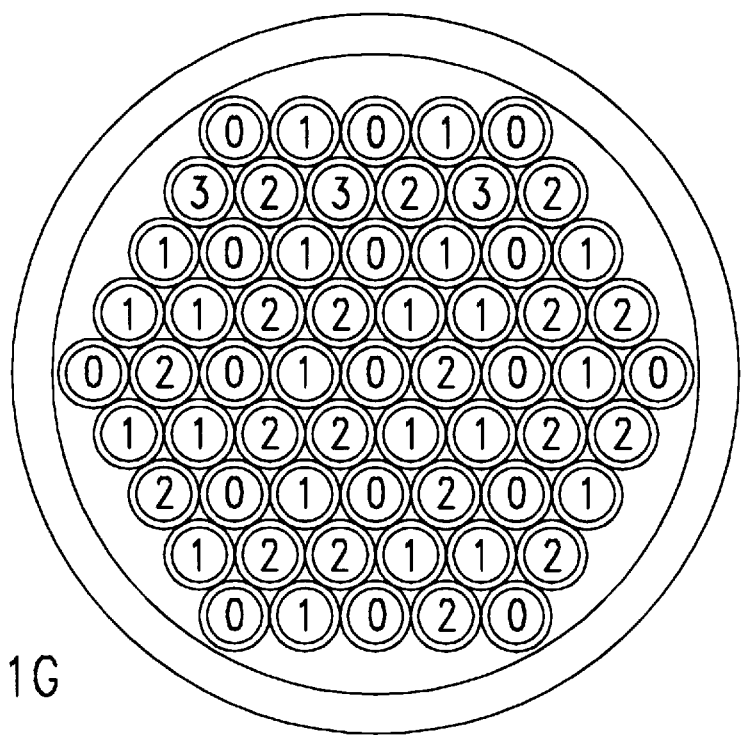
FIG. 1q shows a hexagonal sensitive probe tip of circular shape comprising fibers of two types (0,1).
Figure 1Q:
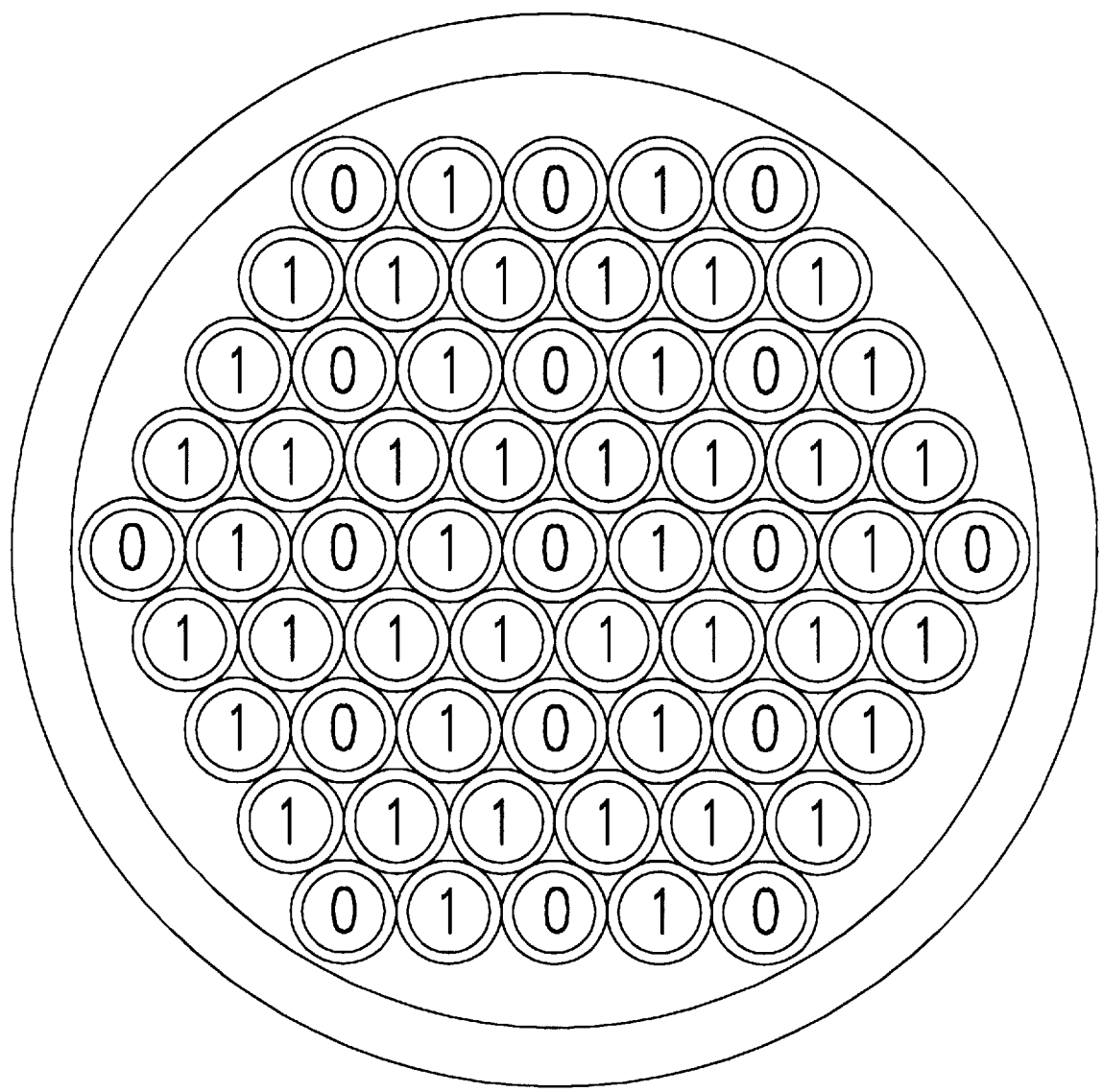

FIG. 1d shows another preferred embodiment of multichannel optical fiber bundle of hexagonal type having a circular cross section of sensitive probe tip. A sensitive probe tip of hexagonal bundle having only three channels is shown in FIG. 1e. Here each light transmission fiber 0 is surrounded with three fibers of type 1 and three fibers of type 2. FIG. 1f shows the sensitive probe tip of a hexagonal bundle having four channels when each light transmitting fiber is surrounded with two fibers of each type 1, 2 and 3. FIG. 1q shows the sensitive probe tip of a hexagonal bundle having only two channels where one light transmitting fiber 0 is surrounded with six light receiving fibers.

Figure 2A:
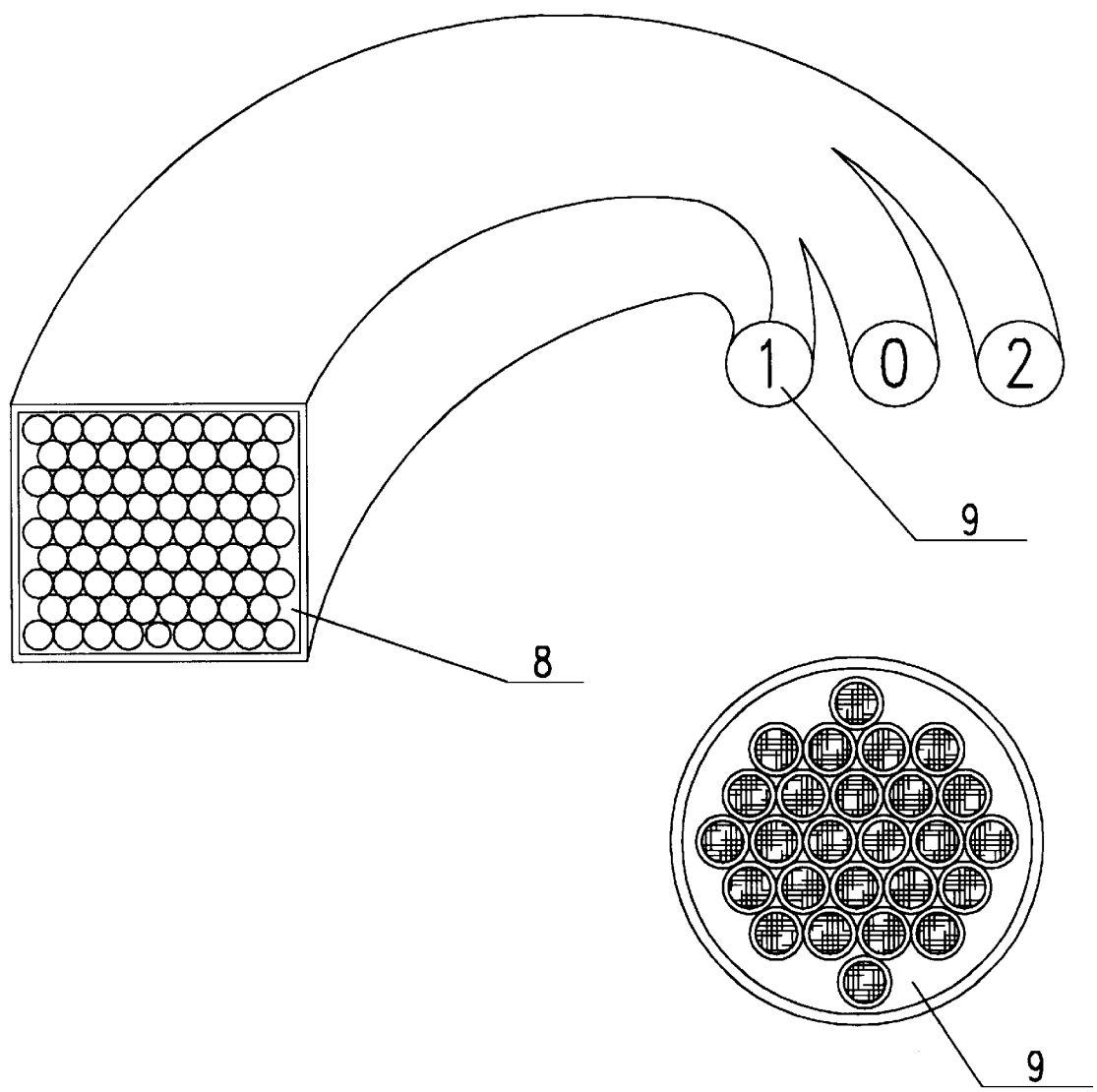
FIG. 2a shows a multichannel bundle of hexagonal type having one light transmitting channel 0 and two light receiving channels 1 and 2.
Figure 2B:
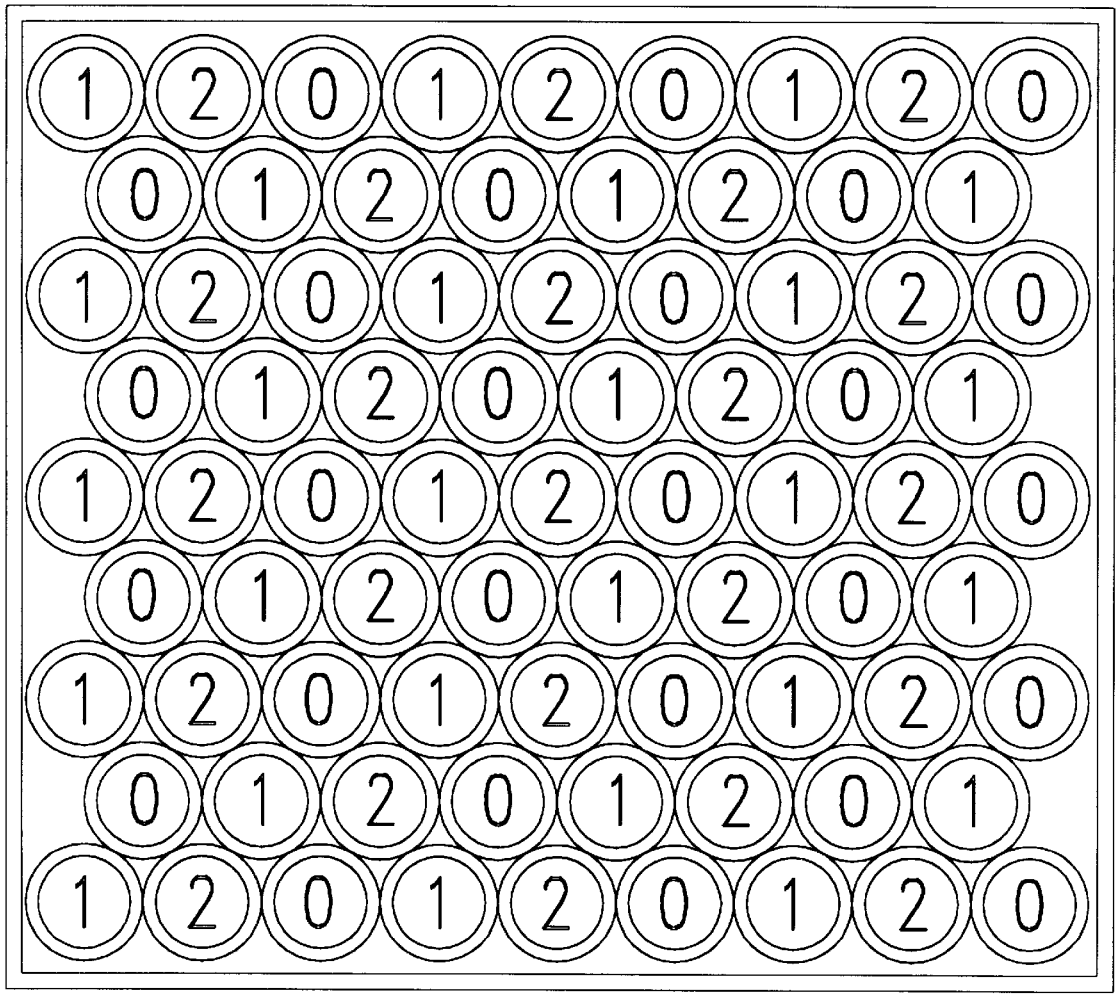
FIG. 2b shows a modification of a sensitive probe tip.

Another preferred embodiment of hexagonal optical fiber bundle 8 having one light transmitting and two light receiving channels 9 is shown in FIG. 2a. FIG. 2b shows a sensitive probe tip of such a bundle when each light transmitting fiber 0 is surrounded with three light receiving fibers belonging to different channels 1 and 2.

Figure 3A:
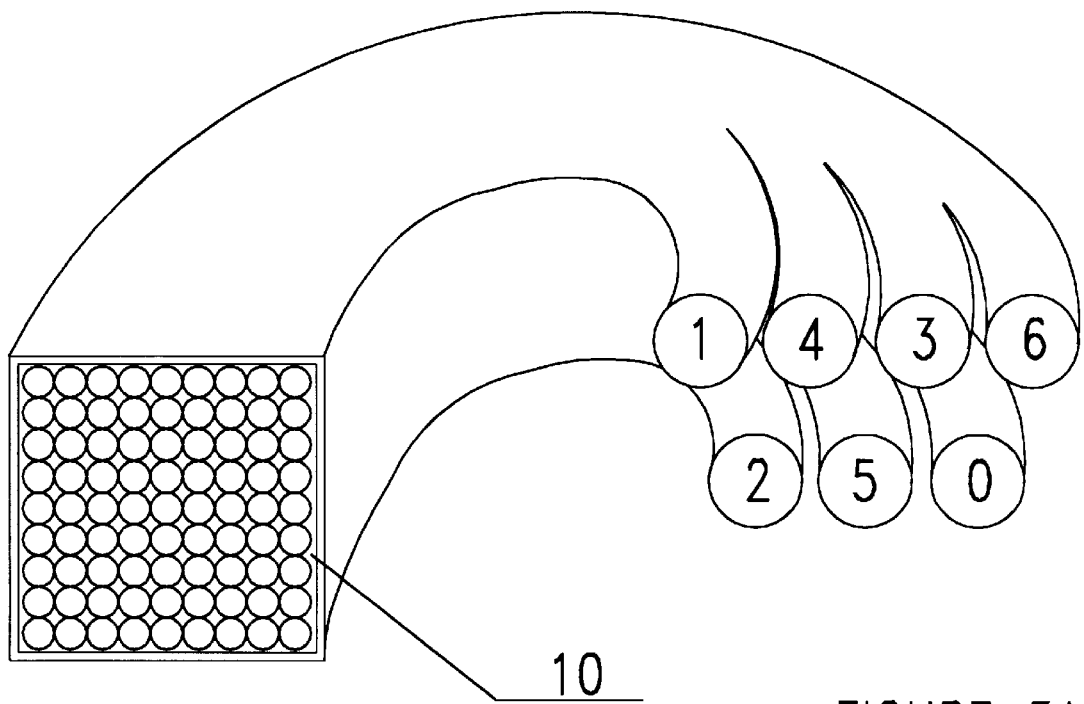
FIG. 3a shows a multichannel bundle of linear type having seven channels numbered from 0 to 6.

FIG. 3a shows an optical fiber bundle in the case of orthogonal (rectangular) ordering of fibers in sensitive probe tip 10. This case is more preferable when fibers in a bundle have very small diameters and for technological reasons they can not be placed in the sensitive probe tip with hexagonal ordering. For example, in the case of fibers having very small diameters glue layer thickness between each two fibers becomes comparable with diameter of the fibers and a third fiber can not be placed between these two preceding fibers, as it is required for hexagonal ordering.

Figure 3B:
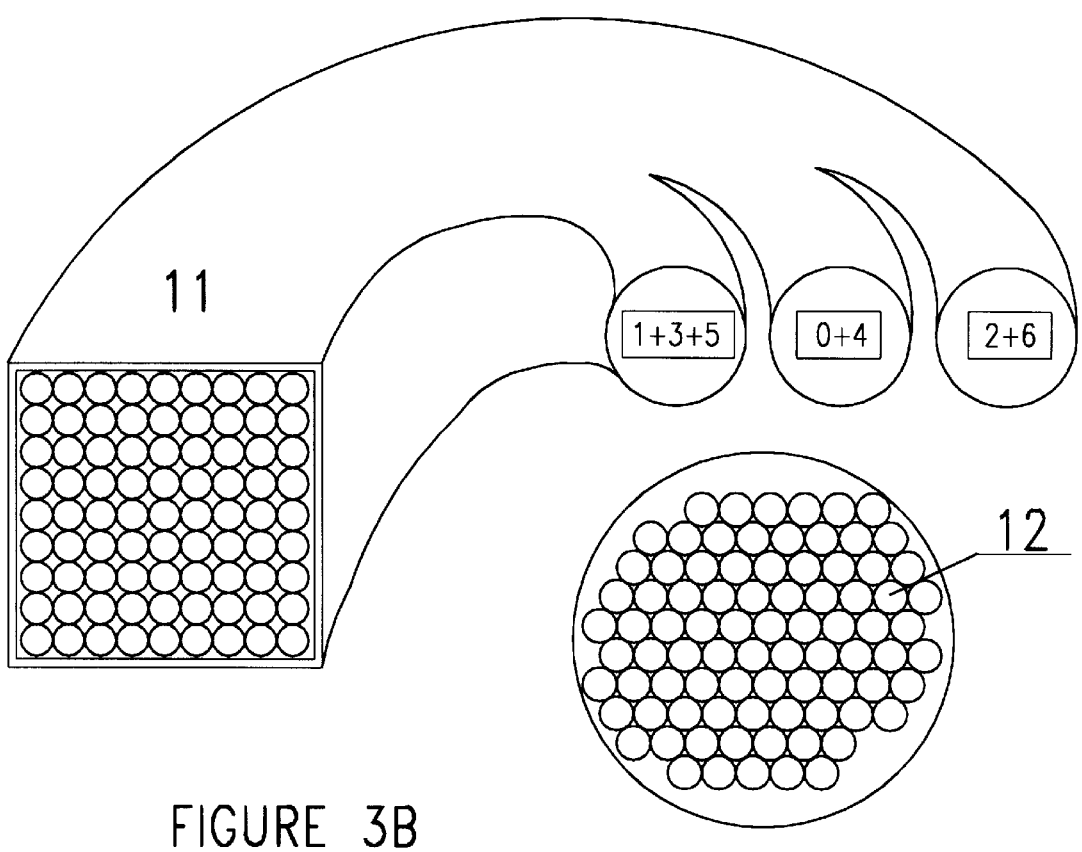
FIG. 3b shows a multichannel bundle of linear type having seven types of fibers is (0, . . . 6) combined into three channels comprising the following fibers: (1,3,5), (0,4), and (2,6).

FIG. 3b shows an example of the bundle having three channels including equal amount of fibers 0, 4 and 2, 6 having symmetrical position in bundle sensitive probe tip 11 around the fibers 1, 3, 5 included into the third channel.

Figure 3C:
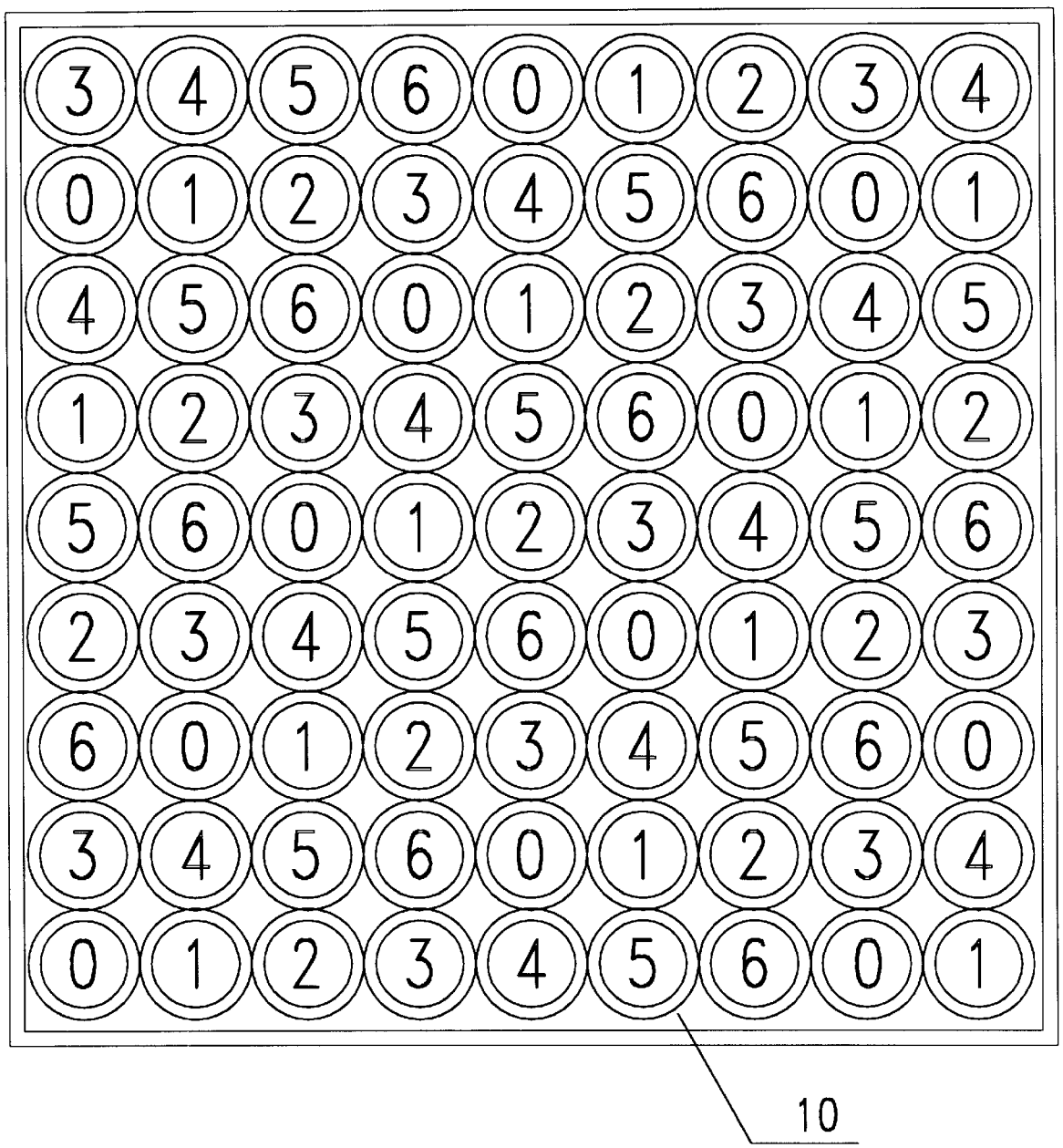
FIG. 3c shows a sensitive probe tip ordered by two-dimensional logic into seven channels (0–6).

FIG. 3c shows a sensitive probe tip 10 of the bundle with seven randomized channels designed for sensor applications. In the case when sensitive probe tip 10 contains a large number of optical fibers, all fibers included in each channel are almost homogeneously distributed over a cross section of sensitive probe tip 10. If one select an arbitrary round spot including a group containing from seven to nine fibers, then such a group will include at a minimum most of the seven kinds of fibers in the bundle. This structure can be used to maximize randomization between different fibers included in one channel. All seven channels of the bundle contain the same amount of fibers having the same degree of randomization. Therefore, the effect of inhomogeneity of the bundle illumnination over its cross section can be minimized.

Figure 3D:
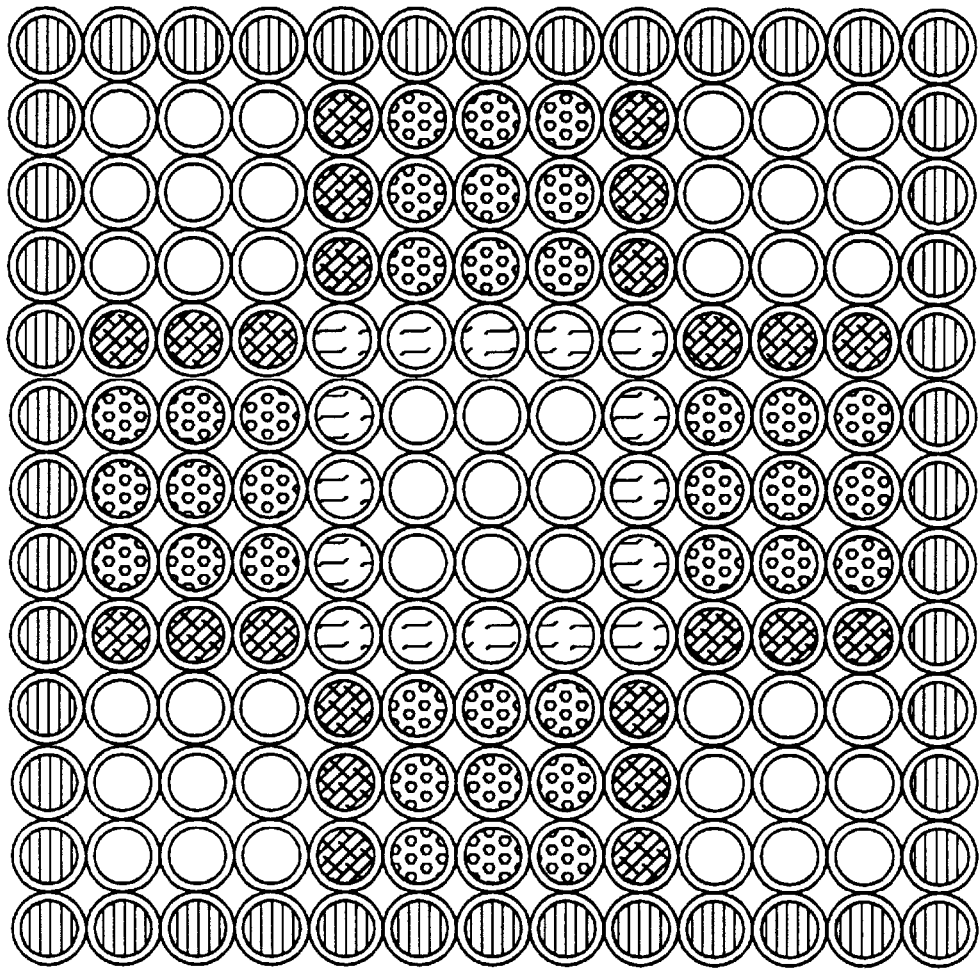
FIG. 3d shows sensitive probe tip ordered by two-dimensional logic and having a 3×3 matrix structure, where $F_0$ is light transmitting fiber, $F_1$–$F_4$ are four main light receiving fibers, $F_5$, $F_6$, $F_7$ are three supplementary light receiving fibers. This sensitive probe is designed to be used in optical fiber sensors for displacement measurement.
Figure 3D:
Figure 3D:
Figure 3D:
Figure 3D:
Figure 3D:

FIG. 3d shows another sensitive probe tip designed for measurement of displacements and two angle deviations. It has five light transmitting channels (fibers $F_0$), four light receiving channels (fibers $F_1$–$F_4$) and three additional light receiving channels (fibers $F_5$–$F_7$) for adjusting reflecting light. The sum of intensities received from fibers $F_1$–$F_4$ is a function of the distance between sensitive probe tip and a reflecting surface of a target. The comparison of light intensities between channels 1–3 and 2–4 provides an information about two angles of inclination between the sensitive probe tip and light reflecting surface. This type of sensitive probe tip is described in detail in U.S. patent (Danielian). The sensitive probe tip can be made very compact. For example, if the diameter of each fiber is 50 μm, the total size of the sensitive probe tip can be as small as 0.7×0.7 mm.

Another preferred embodiment of the multichannel fiber is shown in FIG. 4 a–c. The bundle shown in FIG. 4a has a linear structure of the fibers in its sensitive probe tip 13 and in its output channels 14. An algorithm for ordering the sensitive probe tip includes the following steps:

a linear ordering into the first group $M_1$ of the fibers numbered from 1 to N ( the number N can be as large as 10,000);

a linear ordering into group $M_2$ the next N fibers;

this procedure should be continued up to group $M_j$, where $M_j$ can be usually between 1 and 100 depending also on fiber diameter and parameter N.

a linear ordering of the fibers into output channels which can include either the same linearly arranged fibers 1–N (as shown in FIG. 4a) or the same fibers 1–N arranged in a matrix structure 17 ( as shown in FIG. 4b).

A structure of sensitive probe tip 16 for optical bundle with linearly arranged fibers is shown in FIG. 4c.

Figure 5:
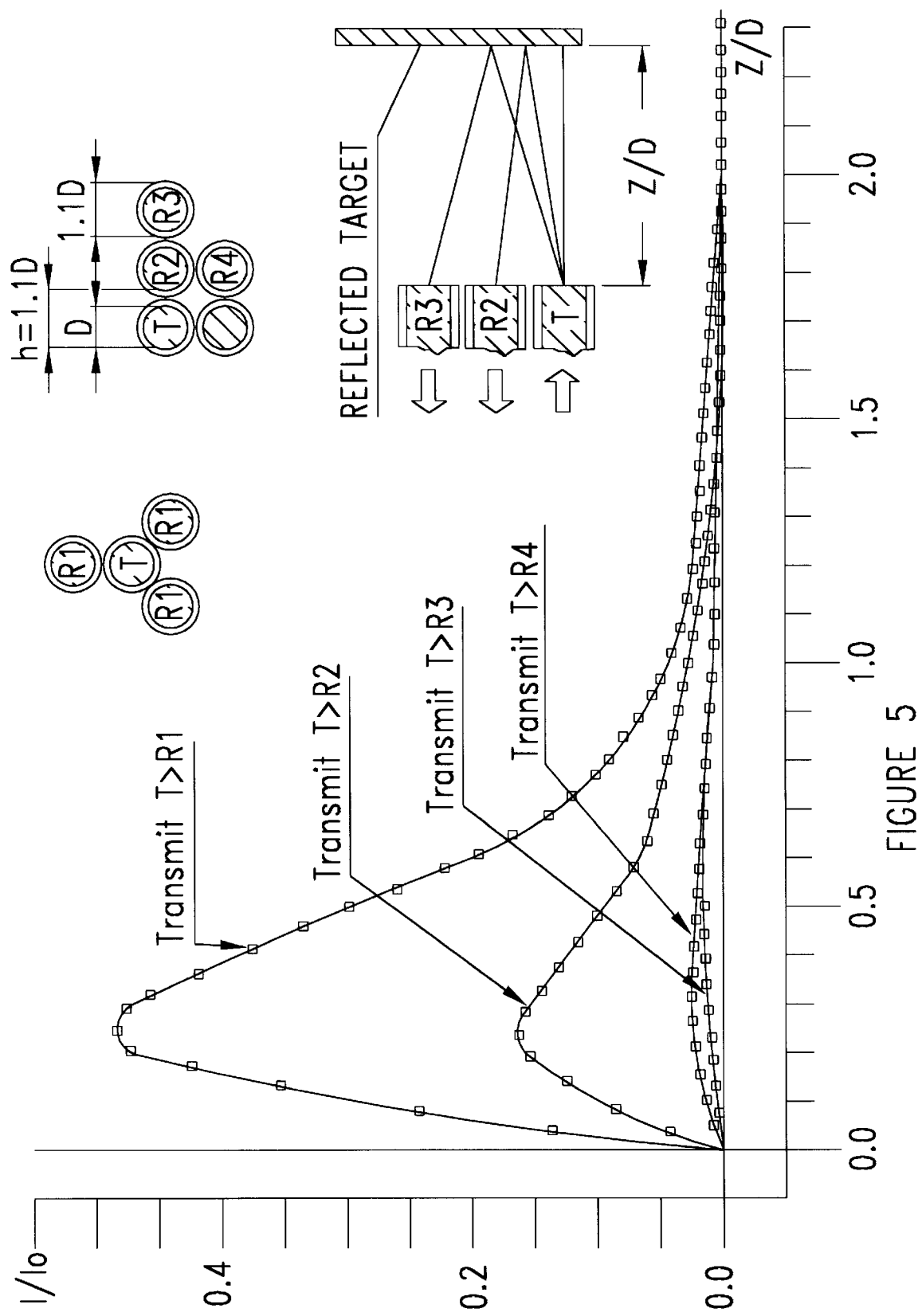
FIG. 5 shows the normalized intensity $I/I_0$ of the light reflected from a mirror as a function of normalized distance Z/D from the mirror for different relative positions of light transmitting and light receiving fibers.
Figure 6:
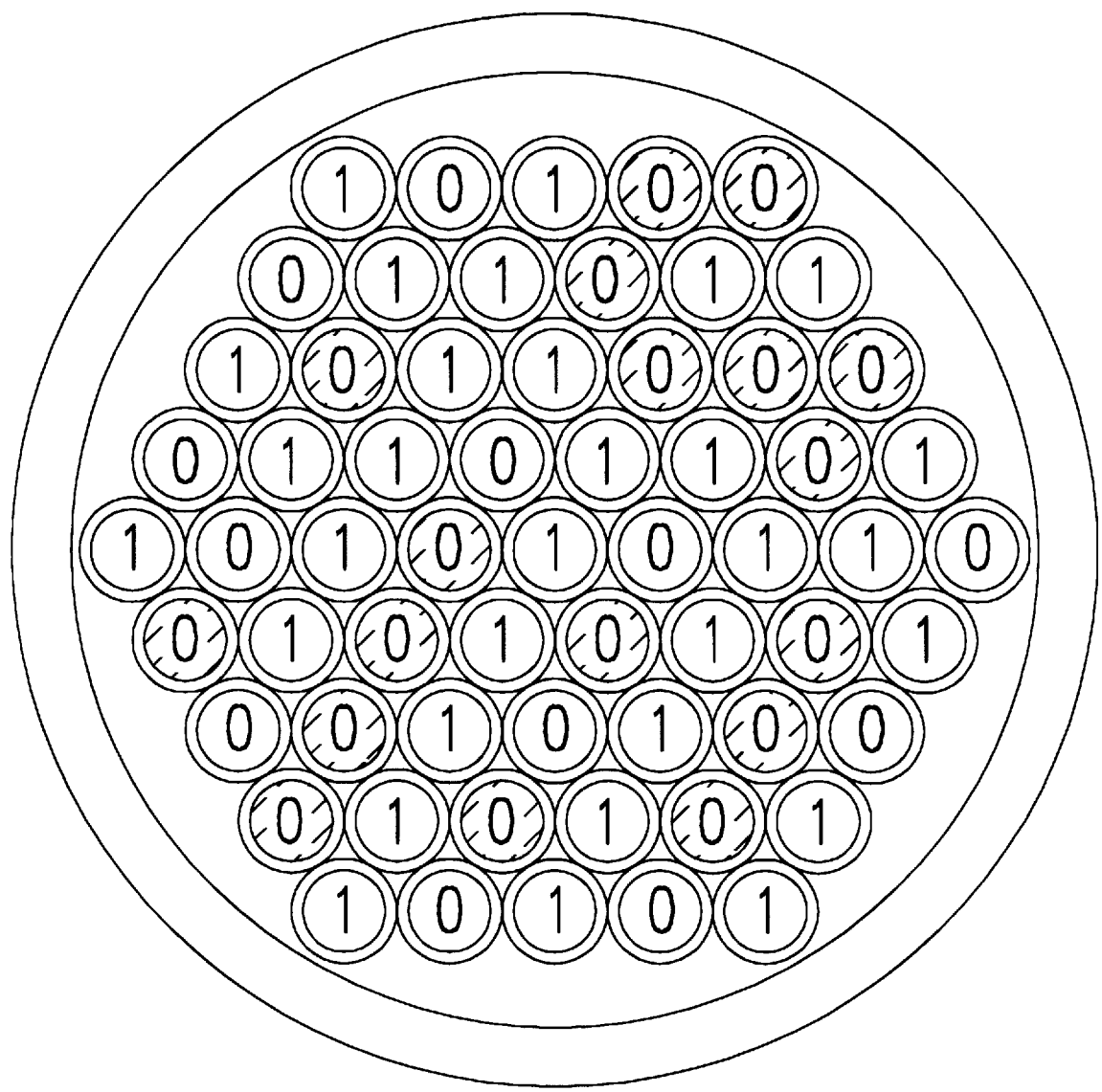
FIG. 6 shows a sensitive probe tip of the bundle comprising two channels arranged into a particular type of structure called "paper and salt structure".

FIG. 5 shows relative intensity of transmitted light $I/I_0$ as a function of normalized distance z/D (D is the fiber core diameter) between fiber end face and light reflecting surface for different relative position of light transmitting fiber T and light receiving fibers $R_1$, $R_2$, . . . $R_4$ which are also shown in FIG. 5. Graphs corresponding to transmission from fiber T into three receiving fibers $R_1$ shows the sum of the intensities in all three receiving fibers as a function of the normalized distance while other graphs show the similar dependencies for intensities in each light receiving fibers $R_2$–$R_4$.

In the case of usual randomization called as "pepper and salt" structure (shown in FIG. 7), the total light intensity reflected into a plurality of light receiving fibers is a sum of all possible combinations of intensities shown in graphs of FIG. 5., while the maximum sensitivity corresponds to the case when the light receiving fiber is placed snugly near the light transmitting fiber. The sensitivity can still be increased in the case when a number of light receiving fibers are placed at the vicinity of the light transmitting fiber as shown in FIG. 5. Employing several light receiving fibers also provides a possibility of speckle noise reduction by averaging the contributions from different speckles.

Figure 7A:
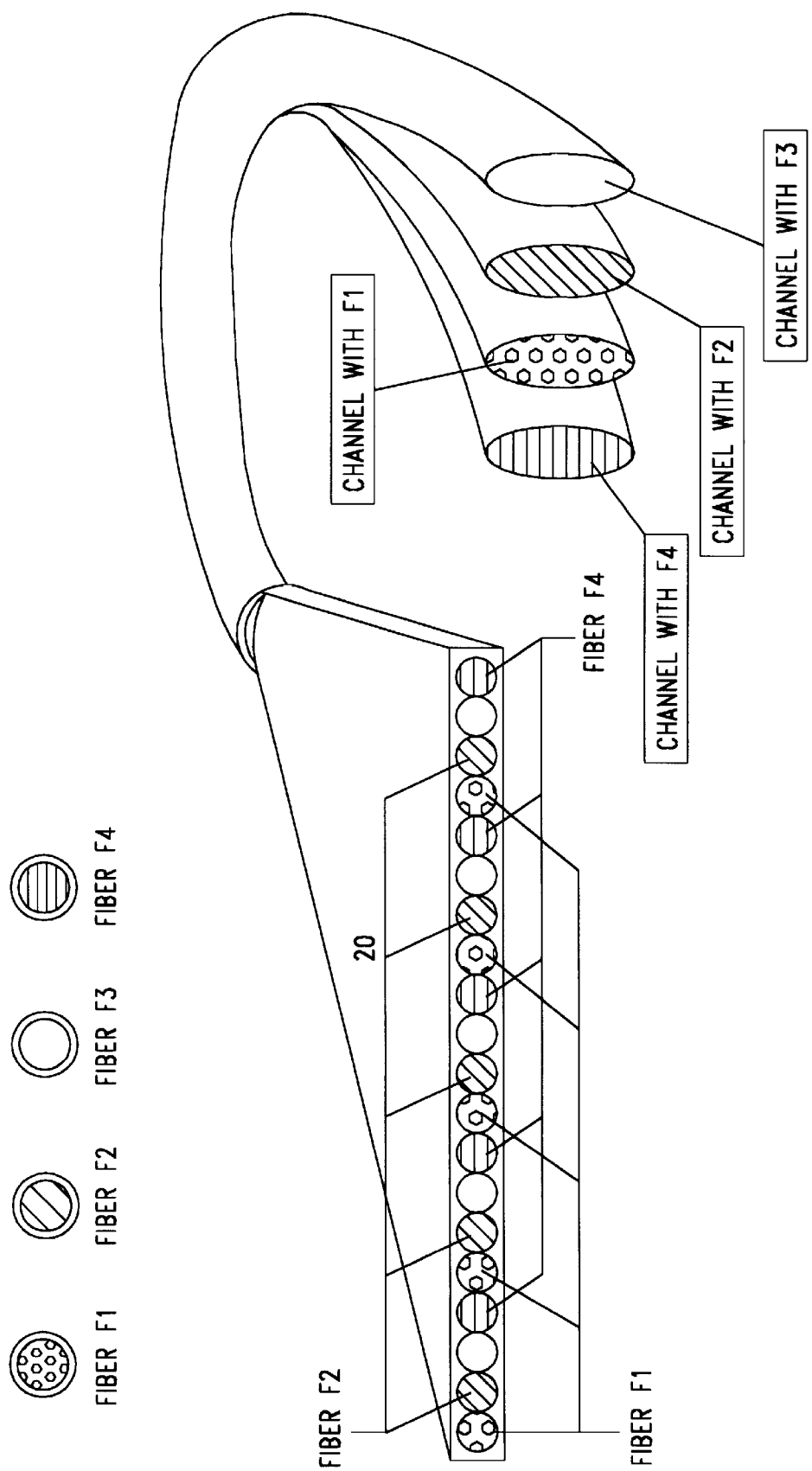
FIG. 7a shows a linear arranged multichannel optical fiber bundle having four channels.
Figure 8:
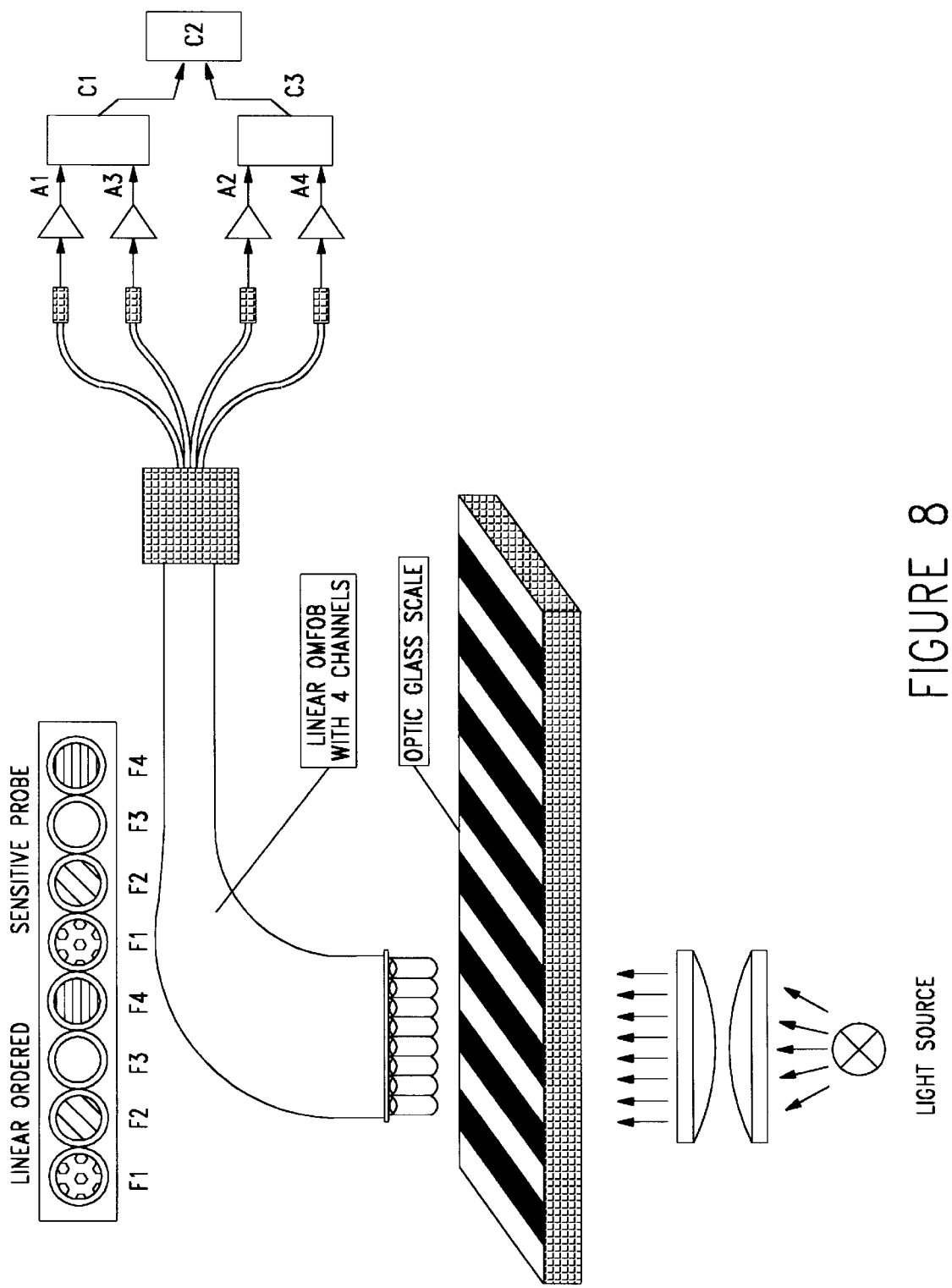
FIG. 8 shows schematics of linear arranged multichannel optical fiber bundle used as a linear displacement encoder (sensor).

The multichannel optical fiber bundles can be designed to have either a linear or a two-dimensional structure. The linear bundles shown in FIG. 7.a,b can be used for different sensor applications. The fibers linearly arranged in a sensitive probe tip are bundled according to some prescribed rule into either layer structure 20 or matrix structure 21 including different combinations of the channels. FIG. 7a shows one preferred embodiment of such a bundle having linear probe tip 20. Four light receiving channels bundled the fibers of types $F_1$, $F_2$, $F_3$, $F_4$ are used as a sensitive probe in a linear encoding sensor. These four types of fibers $F_1$, $F_2$, $F_3$, $F_4$ are first placed in linear sensitive probe tip serially and then repeated N times (the number N can be very large, for example 1024). Since individual fibers in the row have prescribed positions, this sensitive probe tip can be used to detect a position of a linear scale as illustrated in FIG. 8.

The linear multichannel bundles can also be used for other applications such as transferring of four colors from different light sources to one target surface. If channels $F_1$–$F_4$ are connected to light sources with different colors, then switching on and off some of the channels results in a variation of the complete color of the output light.

Figure 9A:
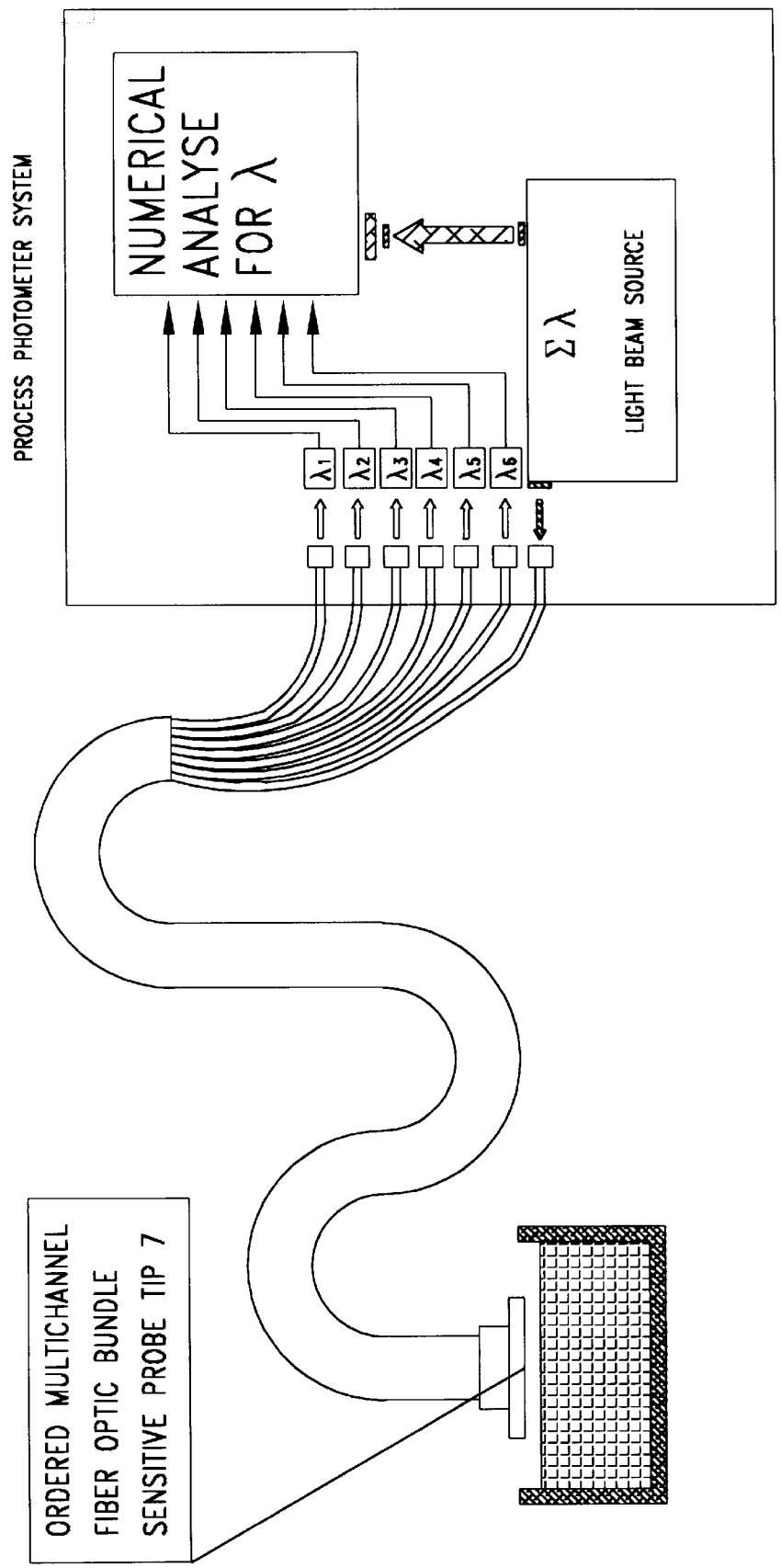
FIG. 9a shows a schematic of a seven-channel optical fiber bundle used for spectrum analysis in a process photometer system.
Figure 9B:
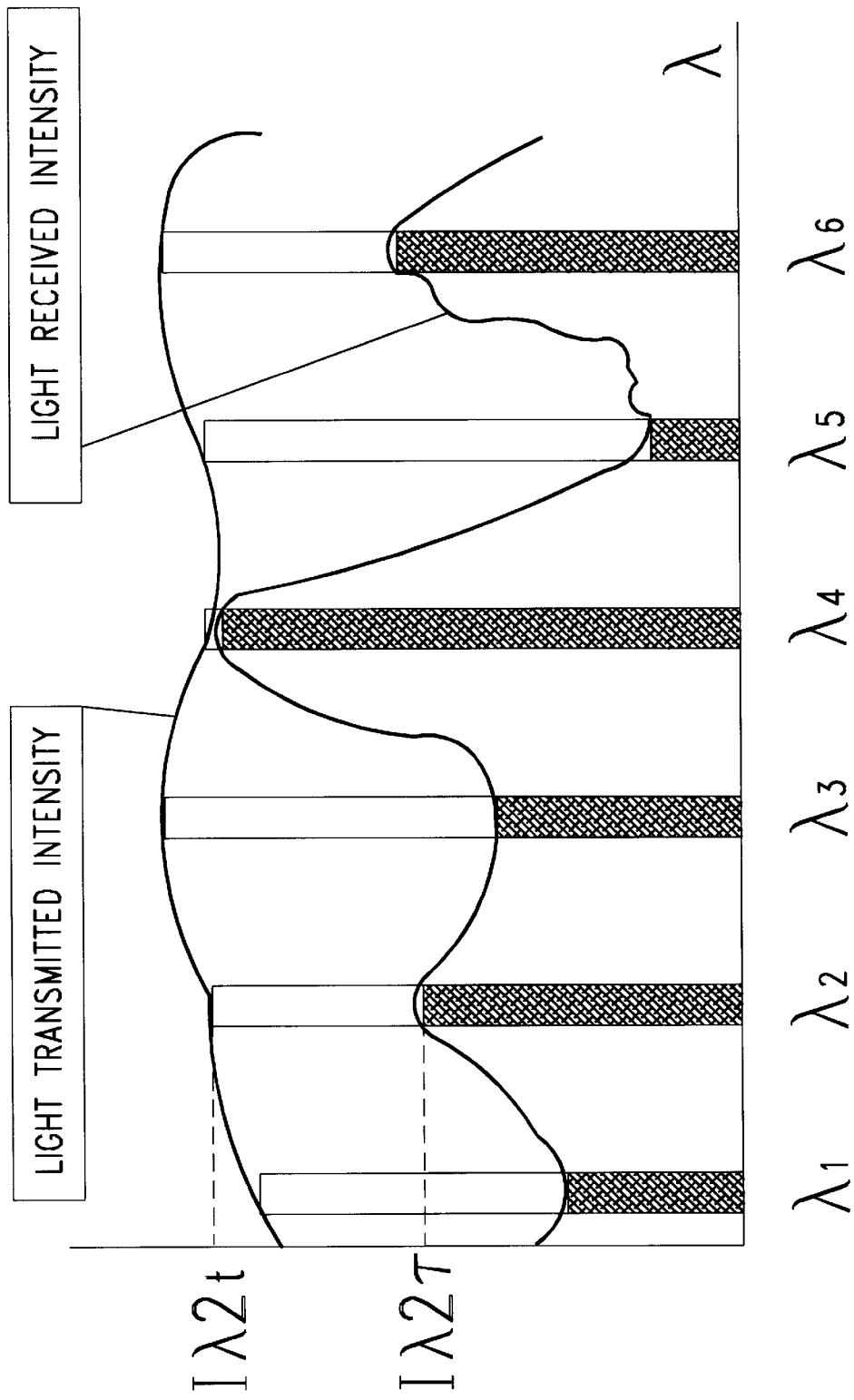
FIG. 9b shows how six wavelengths can be analyzed numerically by this device.

Moreover, the same multichannel light receiving bundle can be used for spectral analysis applications. For example, such optical bundles can be employed instead of arrays of photodetectors which are usually used in spectrum analyzers. Many arrays of photodetectors can not be snugly located near each other as required for improving performance of the spectrum analyzer. The optical fiber bundle can be made very compact. Each group of fibers having prescribed positions of their ends in the sensitive probe tip delivers the light to a specific photodetector for its numerical processing as illustrated in FIG. 9a,b.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A flexible, multichannel optical fiber bundle for optical signal transmission and remote sensing applications which has reduced speckle noise and enhanced homogeneity of light intensity distribution between individual fibers of similar type comprising:
   a sensitive probe tip in which optical fibers are combined and said fibers have positions of their ends ordered within said probe tip;
   at least two remote ends of said bundle, each bundle end having light transmitting fiber channels and light receiving fiber channels, wherein said fiber channels have fiber ends that are ordered in said probe tip using a two dimensional pattern and wherein fibers selected for said channels are randomized within said channel;
   each fiber present in said probe tip is bundled into a prescribed channel;
   fibers within a fiber channel are ordered at said probe tip so that their positions form a structure wherein correlation between fibers of a given fiber type placed in different fiber channels is at a maximum or minimum; and
   whereby said optical fiber bundle exhibits reduced speckle noise resulting from spatial inhomogeneity and asymmetry of radiation of specific fibers within said bundle.

2. A flexible, multichannel optical fiber bundle according to claim 1, wherein said ordering of fiber ends within said probe tip is chosen to be random.

3. A flexible, multichannel optical fiber bundle according to claim 1, wherein said two dimensional pattern of ordering said fiber channels in said probe tip is a hexagonal pattern.

4. A flexible, multichannel optical fiber bundle according to claim 1, having one transmitting channel and from one to six receiving channels to maximize capability of said probe tip to collect light reflected from a target object, wherein:
   each fiber's position in a receiving channel of said probe tip is randomized in such a way that at least one fiber from said receiving channels is snugly placed in the probe tip near at least one of a plurality of transmitting fibers, and
   correlation of positions at said probe tip of all fibers within said receiving channels is similar.

5. A flexible, multichannel optical fiber bundle of claim 4, having means for hexagonal symmetrical ordering of the fiber ends in said sensitive probe tip and further comprising:
   a light transmitting channel 0 and six light receiving channels 1,2,3,4,5,6;
   a plurality of seven types of fibers, $F_0$, $F_1$, $F_2$, $F_3$, $F_4$, $F_5$, $F_6$, bundled within said channels;
   each transmitting fiber $F_0$ being surrounded by light receiving fibers $F_1$, $F_2$, $F_3$, $F_4$, $F_5$, $F_6$ of said six light receiving channels;
   ends of said fibers being arranged in said sensitive probe tip as an ordered matrix structure, having up to $M_1+1$ fibers in a row and up to $M_2$ rows, where $M_1$ and $M_2$ are integers having values up to 10,000; and
   wherein said fiber ends within said sensitive probe tip are arranged so that all said fiber ends follow a pattern selected from the following, a first ordering or a second ordering, wherein said first ordering is given by, a first row comprises fibers- $F_6 - F_5 - F_2 - F_3 - F_5 - F_6 - F_3 - F_2$.....up to $M_1$ fibers,
   a second row comprises fibers- $F_1 - F_0 - F_4 - F_1 - F_0 - F_4 - F_0$.....up to $(M_1 + 1)$ fibers,
   a third row comprises fibers- $F_2 - F_3 - F_6 - F_5 - F_3 - F_2 - F_5 - F_6$.....up to $M_1$ fibers,
   a fourth row comprises fibers- $F_4 - F_0 - F_1 - F_0 - F_4 - F_0 - F_1$....up to $(M_1 + 1)$ fibers,
   .....
   .....
   up to row $M_2$, and
   said second ordering is given by,
   a first row comprises fibers- $F_1 - F_0 - F_4 - F_1 - F_0 - F_4 - F_1 - F_0$.....up to $M_1$ fibers,
   a second row comprises fibers- $F_0 - F_2 - F_3 - F_0 - F_2 - F_3 - F_0$.....up to $(M_1 + 1)$ fibers,
   a third row comprises fibers- $F_5 - F_0 - F_6 - F_5 - F_0 - F_6 - F_5 - F_0$.....up to $M_1$ fibers,
   a fourth row comprises fibers- $F_0 - F_4 - F_1 - F_0 - F_4 - F_1 - F_0$.....up to $(M_1 + 1)$ fibers,
   .....
   .....
   up to row $M_2$.

6. A flexible, multichannel optical fiber bundle of claim 4, having means for simultaneous randomization of fiber end positions of light receiving fiber types $F_1$, $F_2$, $F_3$, $F_4$, $F_5$, $F_6$ within said sensitive probe tip and wherein said light receiving channels are from one of the following group;
   one light receiving channel having a plurality of fibers including fibers of type $F_1$, $F_2$, $F_3$, $F_4$, $F_5$, $F_6$, two light receiving channels having two pluralities of fibers including of type $F_1$, $F_3$, $F_5$, and of type $F_2$, $F_4$, $F_6$ in said two receiving channels, and three light receiving channels having three pluralities of fibers of type $F_1$, $F_4$, of type $F_2$, $F_5$ and of type $F_3$, $F_6$ in said three receiving channels.

7. A flexible, multichannel optical fiber bundle of claim 4, having said sensitive tip of a raster type comprising N rows of fiber ends for fibers $F_0$ through $F_{N-1}$ arranged into a $M_3 \times M_4$ matrix with linear logic between light transmitting and light receiving channels, wherein said fiber ends are ordered as follows:
   a first row formed from $M_3$ fibers of type $F_0$;
   a second row formed from $M_3$ fibers of type $F_1$;
   a third row formed from $M_3$ fibers of type $F_2$;
   . . .
   . . .
   up to row N, having $M_3$ fibers of type $F_{N-1}$;
   row N+1 formed from fibers of type $F_0$;

row N+2 formed from fibers of type $F_1$;
row N+3 formed from fibers of type $F_2$;

. . .

. . .

up to row $M_4$, having $M_3$ fibers of type $F_{N-1}$, and wherein $M_4$ is a multiple of N, $M_4 > N$.

8. A flexible, multichannel optical fiber bundle of claim 4, wherein said sensitive tip comprises fiber ends arranged into $M_4$ lines of fibers, $F_1$ through $F_N$, each having Q groups of channels, including N fibers in each channel arranged as follows:

$(F_1, \ldots F_N)_1, (F_1, \ldots F_N)_2, \ldots (F_1, \ldots F_N)_Q$, wherein positions of said fiber ends in said sensitive tip form layers with a constant step and said fibers are joined into a plurality of fibers included in one form N or Q channels.

9. A flexible, multichannel optical fiber bundle according to claim 1, having one transmitting channel and from one to six receiving channels to maximize capability of said probe tip to collect light reflected from a target object, wherein:

each fiber's position in a receiving channel of said probe tip is randomized in such a way that at least one fiber from said receiving channels is snugly placed in the probe tip near at least two of a plurality of transmitting fibers, and correlation of positions at said probe tip of all fibers within said receiving channels is similar.

10. A flexible, multichannel optical fiber bundle of claim 9, having means for hexagonal symmetrical ordering of the fiber ends in said sensitive probe tip and further comprising:

a light transmitting channel 0 and six light receiving channels 1,2,3,4,5,6;

a plurality of seven types of fibers, $F_0, F_1, F_2, F_3, F_4, F_5, F_6$, bundled within said channels;

each transmitting fiber $F_0$ being surrounded by light receiving fibers $F_1, F_2, F_3, F_4, F_5, F_6$ of said six light receiving channels;

ends of said fibers being arranged in said sensitive probe tip as an ordered matrix structure, having up to $M_1+1$ fibers in a row and up to $M_2$ rows, where $M_1$ and $M_2$ are integers having values up to 10,000; and wherein said fiber ends within said sensitive probe tip are arranged so that all said fiber ends follow a pattern selected from the following, a first ordering or a second ordering, wherein said first ordering is given by,

11. A flexible, multichannel optical fiber bundle of claim 9, having means for simultaneous randomization of fiber end positions of light receiving fiber types $F_1, F_2, F_3, F_4, F_5, F_6$ within said sensitive probe tip and wherein said light receiving channels are from one of the following group;

one light receiving channel having a plurality of fibers including fibers of type $F_1, F_2, F_3, F_4, F_5, F_6$, two light receiving channels having two pluralities of fibers including of type $F_1, F_3, F_5$, and of type $F_2, F_4, F_6$ in said two receiving channels, and three light receiving channels having three pluralities of fibers of type $F_1, F_4$, of type $F_2, F_5$ and of type $F_3, F_6$ in said three receiving channels.

12. A flexible, multichannel optical fiber bundle of claim 9, having said sensitive tip of a raster type comprising N rows of fiber ends for fibers $F_0$ through $F_{N-1}$ arranged into a $M_3 \times M_4$ matrix with linear logic between light transmitting and light receiving channels, wherein said fiber ends are ordered as follows:

a first row formed from $M_3$ fibers of type $F_0$;
a second row formed from $M_3$ fibers of type $F_1$;
a third row formed from $M_3$ fibers of type $F_2$;

. . .

. . .

up to row N, having $M_3$ fibers of type $F_{N-1}$;
row N+1 formed from fibers of type $F_0$;
row N+2 formed from fibers of type $F_1$;
row N+3 formed from fibers of type $F_2$;

. . .

. . .

up to row $M_4$, having $M_3$ fibers of type $F_{N-1}$, and wherein $M_4$ is a multiple of N, $M_4 > N$.

13. A flexible, multichannel optical fiber bundle of claim 9, wherein said sensitive tip comprises fiber ends arranged $M_4$ lines of fibers, $F_1$ through $F_N$, each having Q groups of channels, including N fibers in each channel arranged as follows:

$(F_1, \ldots F_N)_1, (F_1, \ldots F_N)_2, \ldots (F_1, \ldots F_N)_Q$, wherein positions of said fiber ends in said sensitive tip form layers with a constant step and said fibers are joined into a plurality of fibers included in one form N or Q channels.

14. A flexible, multichannel optical fiber bundle according to claim 1, having one transmitting channel and from one to six receiving channels to maximize capability of said probe tip to collect light reflected from a target object, wherein:

| | |
|---|---|
| a first row comprises fibers- | $F_6—F_5—F_2—F_3—F_5—F_6—F_3—F_2$.....up to $M_1$ fibers, |
| a second row comprises fibers- | $F_1—F_0—F_4—F_1—F_0—F_4—F_0$.....up to $(M_1 + 1)$ fibers, |
| a third row comprises fibers- | $F_2—F_3—F_6—F_5—F_3—F_2—F_5—F_6$.....up to $M_1$ fibers, |
| a fourth row comprises fibers- | $F_4—F_0—F_1—F_0—F_4—F_0—F_1$....up to $(M_1 + 1)$ fibers, |

.....
.....

up to row $M_2$, and
said second ordering is given by,

| | |
|---|---|
| a first row comprises fibers- | $F_1—F_0—F_4—F_1—F_0—F_4—F_1—F_0$.....up to $M_1$ fibers, |
| a second row comprises fibers- | $F_0—F_2—F_3—F_0—F_2—F_3—F_0$.....up to $(M_1 + 1)$ fibers, |
| a third row comprises fibers- | $F_5—F_0—F_6—F_5—F_0—F_6—F_5—F_0$.....up to $M_1$ fibers, |
| a fourth row comprises fibers- | $F_0—F_4—F_1—F_0—F_4—F_1—F_0$.....up to $(M_1 + 1)$ fibers, |

.....
.....

up to row $M_2$.

each fiber's position in a receiving channel of said probe tip is randomized in such a way that at least one fiber from said receiving channels is snugly placed in the probe tip near at least three of a plurality of transmitting fibers, and correlation of positions at said probe tip of all fibers within said receiving channels is similar.

15. A flexible, multichannel optical fiber bundle of claim 14, having means for hexagonal symmetrical ordering of the fiber ends in said sensitive probe tip and further comprising:

a light transmitting channel 0 and six light receiving channels 1,2,3,4,5,6;

a plurality of seven types of fibers, $F_0$, $F_1$, $F_2$, $F_3$, $F_4$, $F_5$, $F_6$, bundled within said channels;

each transmitting fiber $F_0$ being surrounded by light receiving fibers $F_1$, $F_2$, $F_3$, $F_4$, $F_5$, $F_6$ of said six light receiving channels;

ends of said fibers being arranged in said sensitive probe tip as an ordered matrix structure, having up to $M_1+1$ fibers in a row and up to $M_2$ rows, where $M_1$ and $M_2$ are integers having values up to 10,000; and wherein said fiber ends within said sensitive probe tip are arranged so that all said fiber ends follow a pattern selected from the following, a first ordering or a second ordering, wherein said first ordering is given by,

| | |
|---|---|
| a first row comprises fibers- | $F_6-F_5-F_2-F_3-F_5-F_6-F_3-F_2$.....up to $M_1$ fibers, |
| a second row comprises fibers- | $F_1-F_0-F_4-F_1-F_0-F_4-F_0$.....up to $(M_1+1)$ fibers, |
| a third row comprises fibers- | $F_2-F_3-F_6-F_5-F_3-F_2-F_5-F_6$.....up to $M_1$ fibers, |
| a fourth row comprises fibers- | $F_4-F_0-F_1-F_0-F_4-F_0-F_1$....up to $(M_1+1)$ fibers, |

.....
.....
up to row $M_2$, and
said second ordering is given by,

| | |
|---|---|
| a first row comprises fibers- | $F_1-F_0-F_4-F_1-F_0-F_4-F_1-F_0$.....up to $M_1$ fibers, |
| a second row comprises fibers- | $F_0-F_2-F_3-F_0-F_2-F_3-F_0$.....up to $(M_1+1)$ fibers, |
| a third row comprises fibers- | $F_5-F_0-F_6-F_5-F_0-F_6-F_5-F_0$.....up to $M_1$ fibers, |
| a fourth row comprises fibers- | $F_0-F_4-F_1-F_0-F_4-F_1-F_0$.....up to $(M_1+1)$ fibers, |

.....
.....
up to row $M_2$.

16. A flexible, multichannel optical fiber bundle of claim 14, having means for simultaneous randomization of fiber end positions of light receiving fiber types $F_1$, $F_2$, $F_3$, $F_4$, $F_5$, $F_6$ within said sensitive probe tip and wherein said light receiving channels are from one of the following group;

one light receiving channel having a plurality of fibers including fibers of type $F_1$, $F_2$, $F_3$, $F_4$, $F_5$, $F_6$, two light receiving channels having two pluralities of fibers including of type $F_1$, $F_3$, $F_5$, and of type $F_2$, $F_4$, $F_6$ in said two receiving channels, and three light receiving channels having three pluralities of fibers of type $F_1$, $F_4$, of type $F_2$, $F_5$ and of type $F_3$, $F_6$ in said three receiving channels.

17. A flexible, multichannel optical fiber bundle of claim 14, having said sensitive tip of a raster type comprising N rows of fiber ends for fibers $F_0$ through $F_{N-1}$ arranged into a $M_3 \times M_4$ matrix with linear logic between light transmitting and light receiving channels, wherein said fiber ends are ordered as follows:

a first row formed from $M_3$ fibers of type $F_0$;
a second row formed from $M_3$ fibers of type $F_1$;
a third row formed from $M_3$ fibers of type $F_2$;
. . .
. . .
up to row N, having $M_3$ fibers of type $F_{N-1}$;
row N+1 formed from fibers of type $F_0$;
row N+2 formed from fibers of type $F_1$;
row N+3 formed from fibers of type $F_2$;
. . .
. . .
up to row $M_4$, having $M_3$ fibers of type $F_{N-1}$, and wherein $M_4$ is a multiple of N, $M_4 > N$.

18. A flexible, multichannel optical fiber bundle of claim 14, wherein said sensitive tip comprises fiber ends arranged into $M_4$ lines of fibers, $F_1$ through $F_N$, each having Q groups of channels, including N fibers in each channel arranged as follows:

$(F_1, \ldots F_N)_1, (F_1, \ldots F_N)_2, \ldots (F_1, \ldots F_N)_Q$, wherein positions of said fiber ends in said sensitive tip form layers with a constant step and said fibers are joined into a plurality of fibers included in one form N or Q channels.

* * * * *